United States Patent [19]

Kantner

[11] 4,211,749

[45] Jul. 8, 1980

[54] LIQUID CONTAINER FOR URINE COLLECTION

[76] Inventor: Hans-Joachim Kantner, Fichtwenweg 5, D-6072 Dreieichenhain, Fed. Rep. of Germany

[21] Appl. No.: 751,157

[22] Filed: Dec. 16, 1976

[30] Foreign Application Priority Data

Feb. 25, 1977 [DE] Fed. Rep. of Germany ....... 2556636

[51] Int. Cl.[2] ........................ G01N 33/16; G01N 1/10; E03D 13/00

[52] U.S. Cl. .................................... 422/102; 128/760; 215/10

[58] Field of Search .................. 23/259, 292; 128/2 F, 128/295; 422/102; 215/10

[56] References Cited

U.S. PATENT DOCUMENTS

| | | | |
|---|---|---|---|
| 2,077,027 | 4/1937 | Torras | 215/10 |
| 2,488,611 | 11/1949 | Stallings | 215/10 |
| 2,564,834 | 8/1951 | Devine et al. | 215/10 |
| 2,960,248 | 11/1960 | Kuhlman | 215/10 |
| 3,001,564 | 9/1961 | Hopkins | 215/10 |
| 3,162,327 | 12/1964 | Bennett | 215/10 |
| 3,243,068 | 3/1966 | Huston | 215/10 |
| 3,369,687 | 2/1968 | Walls | 215/10 |
| 3,623,634 | 11/1971 | Norgard | 215/10 |
| 3,625,654 | 12/1971 | Van Duyne | 23/259 X |
| 3,635,091 | 1/1972 | Linzer et al. | 128/2 F |
| 3,699,815 | 10/1972 | Holbrook | 128/2 F |
| 3,711,871 | 1/1973 | Sherin | 128/295 |
| 3,781,922 | 1/1974 | Ericson | 128/2 F |
| 3,811,136 | 5/1974 | Whitney et al. | 128/2 F |
| 3,830,107 | 8/1974 | Linzer et al. | 128/2 F |
| 3,888,236 | 6/1975 | Marx | 128/2 F |
| 3,929,412 | 12/1975 | Villari | 23/259 |
| 4,013,077 | 3/1977 | Ritota | 128/295 |

*Primary Examiner*—R. E. Serwin
*Attorney, Agent, or Firm*—Jacobi, Lilling & Siegel

[57] ABSTRACT

Disclosed is a container for liquids, especially urine, with a lid which includes a spout. The upper and lower ends of the container are shaped complementarily to facilitate nesting of successive containers on top of one another. The spout is guarded by an upper nesting container, and, in some embodiments, may be or form part of the upper nesting formation.

34 Claims, 10 Drawing Figures

FIG.1
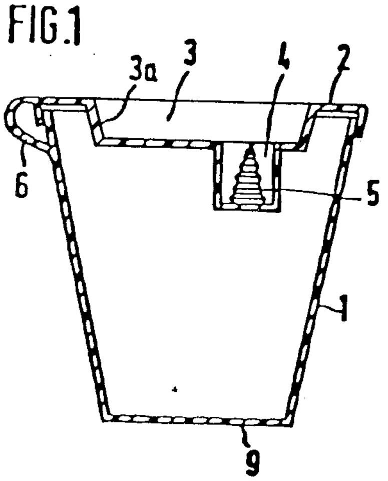
FIG.2
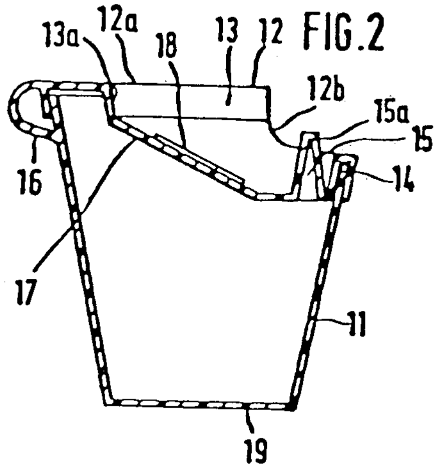
FIG.3
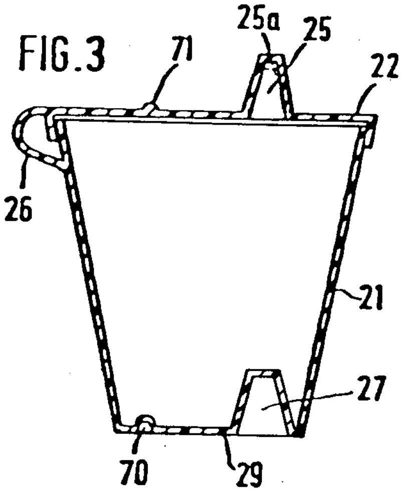
FIG.4
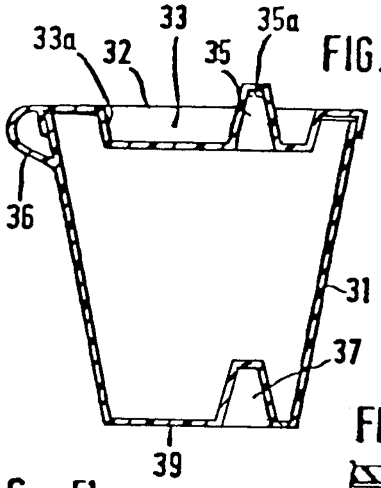
FIG.5
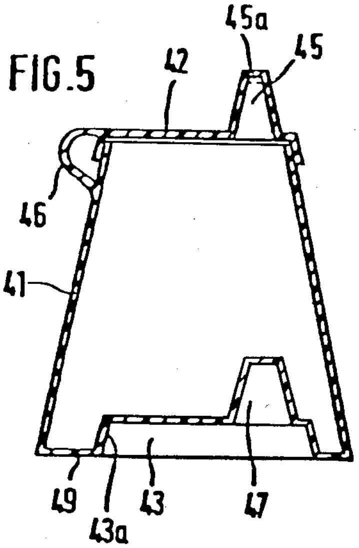
FIG.6
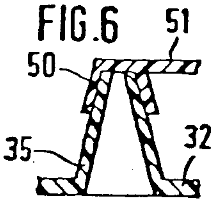
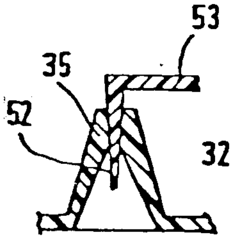
FIG.7
FIG.8
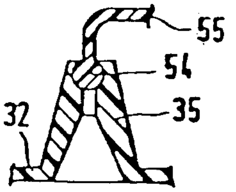
FIG.9
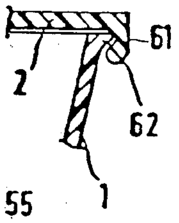
FIG.10
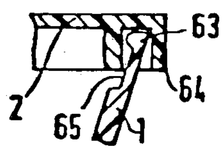

LIQUID CONTAINER FOR URINE COLLECTION

The invention relates to a beaker with a lid for the reception of fluids, more especially urine, the lid comprising a spout.

There is known a plastic beaker whose lid, which is integrally connected thereto through a link, comprises a spout projecting from its edge contour which is uppermost in the operational condition. This known beaker has a round cross-sectional contour and an internal diameter on the beaker edge which is larger than that on the beaker base.

Such known beakers are intended for the reception of urine for the performance of laboratory or clinical urine tests in order to find out the status thereof, and for this purpose it should be possible not only to fill them easily and conveniently with urine but also to keep them tightly sealed after filling until a removal of urine or the introduction of a test strip into the beaker contents is required for the performance of the respective tests. It should be possible to carry out these two steps quickly and easily and yet hygienically. The beaker with its lid should be a cheap vessel which can be thrown away when the urine tests have been completed.

It has turned out that such known beakers have a number of disadvantages which impede the working pattern to quite a considerable extent, particularly in the laboratory operation of major test laboratories or in clinics where urine specimens to be tested involve a fair amount of time. The most serious disadvantage is the increased space requirement for filled sealed beakers resulting from the fact that these can always only be placed side by side because the free end of the spout projects upwardly from the lid edge contour. This disadvantage has a particularly unpleasant effect when the respective tests have been performed, because the filled beakers now have open spouts and, when a plurality of such beakers, which have already undergone tests, are positioned over a wide area awaiting transportation to the disposal station, and more especially during transportation thereof, there is a danger of one or the other of these beakers overturning and its contents passing through the open spout. Furthermore, the plurality of open spouts is a source of impairing the hygienic working conditions of the laboratory operation.

The task underlying the invention is, while maintaining the advantages of such a known beaker with respect to its specific use as a container for media endangering hygiene, such as urine, which are not subjected to laboratory tests immediately after filling, but while avoiding the disadvantages thereof, to provide with simple and low-cost means a cheap disposable vessel which can be easily filled and closed in a fluid-tight manner and which allows several vessels according to the invention to be placed or stacked one above the other, so that there results not only a considerable reduction in the space requirement both prior to the performance of the laboratory tests and, in particular, after it but also a considerable lessening in the impairment of hygiene during such laboratory test work, including the transportation of the filled beakers to and from the test station, as well as a considerable lessening of the danger of individual vessels, which are filled but open when the laboratory tests have been performed, being overturned and their contents pouring out.

According to the invention, this task is solved in a surprisingly simple manner in that on a beaker with a lid for the reception of fluids, more especially urine, the lid comprising a spout, the lid comprises on its external side, from which the spout projects, a concavity which corresponds in its contours approximately to the beaker jacket end area near the beaker base and/or the beaker base comprises a concavity which corresponds in its contours approximately to the external side of the beaker.

In this way, the invention allows empty or filled beakers of this construction to be stacked one above the other. What is surprising about this is that it is possible not only to store a plurality of beakers which are thus stacked one on top of the other, whether they are empty or filled, in a space that is considerably smaller than that required for beakers of conventional construction but also to transport them more easily and safely, when one should really have expected that a superimposition of beakers, which is not at all possible with conventional beakers, would result in a greater instability of the combination of the individual units as compared to all of them standing on a common base surface. However, surprisingly, the opposite is the case. To this there is added the effect that each further beaker which is superimposed on a beaker beneath it covers the orifice of the spout, which was open until now, when the laboratory tests have been completed, thus contributing substantially to the increase in hygiene and, in particular, to a reduction of unpleasant smells, in that the number of spout orifices, through which the beaker contents are in contact with the environment, can be drastically reduced by the invention.

Another inventive development is characterised in that the lid comprises a shoulder which extends along its periphery and is pulled up towards the exterior and has an internal contour that corresponds approximately to the beaker jacket end area near the beaker base. This embodiment of the invention provides, with particularly simple means, which can be realised productionwise without any difficulties and which are therefore extremely economical, a preferred solution of the basic task not only to enable at all a superimposition of two beakers, which are closed by their associated lids, but also to fix in a positive manner the upper beaker placed on the lower beaker against a lateral displacement, approximately parallel to its beaker base plane.

A development of this inventive concept is characterised in that the lid comprises an approximately chamber-like indentation, which is open towards the exterior and in which an approximately concertina-like, foldable spout is sunk in its condition of rest and can be pulled out for its operating condition. This embodiment is particularly suitable if it is desired that for some reason or other the beaker base should not comprise any convexities which project substantially into the beaker interior, so that there is also no space available into which a spout projecting from the lid of another beaker towards the top could project, so as to allow the two beakers to be superimposed. In this embodiment of the invention the spout is pushed into the chamber-like indentation of the lid of the lower beaker at the latest through the superimposition of the upper beaker, due to its base coming into contact with the spout tip.

Another subordinate inventive idea is concerned with a beaker according to the invention where the spout is rigidly directed away from the external side of the lid, such as is conventional. According to this further development of the invention, the beaker jacket of such a beaker may be shortened on its upper edge near the lid over a partial area of its periphery, the lid comprising an area corresponding with respect to the size of its centre angle to the unshortened area of the beaker jacket and comprising a concavity whose edge contour is formed by an encircling and outwardly drawn-up shoulder having an internal contour which corresponds approximately to the beaker jacket area that is near the beaker base, as well as an area which corresponds to the shortening of the beaker jacket and in which there is arranged a spout which terminates with its free end beneath the lower limitation of the shoulder in this lid area, corresponding to the unshortened beaker jacket area, but above the limitation of the lid area corresponding to the beaker jacket area comprising the shortening, and whose lower end merges surface-wise in the lid surface leading into the opposite lid edge contour. This exemplified embodiment also allows the beaker base to be constructed without any convexities projecting into the beaker interior, without impairing the solutions of the tasks on which the invention is based, since in the operating condition the upper free end of the spout always comes to lie beneath the external side of the beaker base of a beaker superimposed on its associated lid.

Another subordinate concept of the invention is concerned with the solution of the basic task on a beaker comprising a prior art spout which is rigidly directed away from the external side of the lid beyond the edge contour thereof. In a further development of the invention it is proposed that, with the lid placed on the beaker, sealing the latter, in the operating condition thereof, the beaker base should comprise perpendicularly beneath the spout a concavity corresponding to the spout area projecting over the lid edge contour. Even when it is not intended to change the conventional design of the lid, with the spout projecting beyond its highest edge contour, it is made possible through this inventive idea to stack individual beakers on top of one another along the lines of the invention.

Basically, there is no need to envisage an angle-wise association of the beakers which are arranged one above the other in any of the described preferred embodiments of the invention. According to the task of the invention, it is sufficient if, on the one hand, the possibility of stacking beakers of the type of the known beakers described is provided at all and if, in addition, a reliable fixing of the superimposed beakers is ensured preventing any lateral relative displacement, for example, parallel to their base planes or base surfaces. However, for reasons of an operational rationalisation in the performance of laboratory tests, it has turned out to be preferable if the filled beakers are delivered to and/or removed from the testing equipment in a very specific alignment if this equipment works automatically. In order to provide a simple and economical solution in this event, there is provided, in a further inventive idea which does not develop the invention in an obvious manner, a means for the angle-wise association of the lid and beaker, comprising at least one projection and/or an inward concavity on the lid and, correspondingly, at least one concavity and/or projection on the beaker base. For this purpose, there may be arranged, for example, on the lid small knobs or bosses, projecting from the latter, in a suitable alignment relative to one another, while corresponding receptacles are provided in an identical alignment in the beaker base, so that the knobs or bosses on the lid of a beaker located underneath engage in a centring manner in corresponding recesses in the beaker base of a superimposed beaker. Conversely, it is however also possible for the beaker base to comprise such projecting knobs or bosses in a suitable arrangement and co-ordination, the lid comprising in this case the correspondingly arranged receiving recesses. In such cases, it is even possible, in an embodiment in which the spout projects from the upper edge contour of the lid, for the beaker base to have any type of concavity provided it is ensured that volumewise it is capable of receiving the spout within itself. However, for reasons concerning the material, it will be preferred to design this concavity in the beaker base in a shape that corresponds approximately with the shape of the spout. According to a further perfection of the invention, it may however advantageously be provided that the projection of the associated device which determines the angular association of the lid and beaker is formed by the area of the rigid spout which projects from the lid edge contour. Thus, the spout itself is used as the centring projection. To this end, the associated concavity in the lid base is given an outer contour which is such that the spout of the lid fits therein, at least partially, so that the spout of a beaker located beneath comes to abut, and thus to engage operatively in, the external wall of the beaker base concavity of a superimposed beaker, when two beakers are placed one above the other. In most cases, it has proved to be sufficient if only the spout is utilised as such a centring projection, although applications are conceivable where it may be expedient to provide additionally different centring projections on one part with corresponding recesses on the other part.

Basically, the spout may have a cross section that is approximately constant over its entire length. However, it has proved to be particularly expedient, with respect to easy moulding during the production of the beaker parts and the easiest possible insertion of the spout into a corresponding receiving cavity in the beaker base of a superimposed beaker, in addition to increasing ease and accuracy when the beaker contents are withdrawn through the spout, if the cross section of the spout is tapered towards its free end, at least in a plane containing the central axis of the beaker in the operating condition. Advantageously, the spout may be shaped in known manner substantially like a cone or the frustum of a cone. Furthermore, the spout may advantageously be designed in known manner as a cone or the frustum of a cone having an elongate base surface. These features, which are also known on the conventional beaker, gain a new importance in the invention, as already stated.

On the other hand, the spout may be designed as a pyramid or as the frustum of a pyramid. Particularly preferred is a pyramid or frustum of a pyramid which is oblique over its base surface. It has proved to be particularly advantageous if the spout has an elongate cross-sectional contour in a section directed in the operating condition parallel to the lower edge contour of the beaker base, by which contour the base surface of the latter is determined.

The spout design with a substantially straight-line and angular cross-sectional contour, such as is given on a pyramid or the frustum of a pyramid, is frequently preferable to the design with round areas of the cross-sectional contour when the spout is formed as a part which rigidly projects from the lid and which is used for centring two superimposed beakers or determines this centring on its own, in that it can be brought into operative connection with a correspondingly contoured concavity of the base of the other beaker.

Furthermore, the spout may preferably be arranged in known 'per se' manner near the lid edge. This facilitates handling when the beaker contents are removed.

Furthermore, the beaker edge and the associated part of the lid edge may each comprise a known 'per se' closing means, which are in clamping engagement in the operative condition and seal the beaker interior in a fluid-tight manner. In a further development according to the invention, the closing means may expediently be formed by a bead which is arranged along the beaker edge and which is clamped in the operating condition with a lid edge contour which is approximately hat-shaped in design, so as to be fluid-tight. This ensures a reliable clamping engagement between the lid edge and the beaker edge with an efficient fluid tightness.

In order to prevent the lid or beaker being lost, the lid may furthermore be connected to the beaker in known 'per se' manner by means of a link.

In order to facilitate production, particularly when the beaker is made in known 'per se' manner as an injection-moulded part in plastics material, the filling orifice of the beaker may have, in the interests of a good mouldability thereof, in known 'per se' manner an edge contour that is larger than that of the beaker base. This results in the stability being dependent on the height of the beaker or the filling height of its contents. If a particularly good stability is required, then another inventive development of the invention may expediently be of assistance, according to which the filling orifice of the beaker has an edge contour which is smaller than that of the beaker base. However, with this embodiment it is difficult to produce the beaker as an injection-moulded part, if the beaker is to consist of one part, because it is only with great difficulty that such a part, which widens towards the beaker base, is moulded. Therefore, if such an embodiment is desired, the beaker will either be produced in several parts, the beaker jacket being connected to the beaker base in a suitable manner, or the beaker will be produced in one piece by the blowing process or by another suitable shaping method operating without a core.

Furthermore, the beaker may have a known 'per se' round cross-sectional contour. Particularly when the beaker has to pass on automatically operating delivery conveyors to test equipment, it may be expedient in the interests of a fast and easy automatic alignment of the beaker to be conveyed if its has an approximately elliptical or egg-shaped cross-sectional contour. On the other hand, it may however also have, in a further inventive development, a polygonal, preferably rectangular and more especially square, cross-sectional contour. The last-mentioned embodiment provides the advantage that it does not only contribute to improving the rapidity and ease of the alignment on such conveyors but can be used for centring or aligning beakers which are to be superimposed and that, in addition it is capable of improving the stability of a group of juxtaposed or superimposed beakers to a considerable extent in that such beakers can be supported on one another at least along their upper edge area. The favourable consequence is, according to the task set, a considerable facilitation in the handling of large batches of filled beakers and hence a rationalisation of the laboratory operation.

Basically, it is sufficient for the defined use of a beaker according to the invention if its spout comprises in known 'per se' manner a moulded-on, separable tip, which seals its orifice until the first withdrawal from the beaker contents and which is not separated before the beaker is in the laboratory. However, this embodiment has the disadvantage that once the tip has been separated the beaker contents have free access to the environment, which entails a considerable amount of obnoxious smells from decomposition products in the beaker contents, which may be as defined preferably urine, particularly when a filled beaker which has been opened has to be left for a considerable length of time before another sample of its contents is taken, for example, for another test or when it is conveyed to the disposal station, quite apart from the fact that under these conditions neither a sufficient degree of hygiene nor an adequate sterilitity of the test processes can be ensured.

This is remedied in a surprisingly simple manner by an expedient construction according to a further inventive idea, according to which the spout is sealed in a fluid-tight manner by a closing element which can be removed and put back into its operative position. This closing element may expediently be a clamping cap which covers the free end of the spout. On the other hand, the closing element may be a plug inserted in the free end of the orifice of the spout. This plug may be designed as a strip which tapers slightly towards its free end, which will always be expedient when the spout orifice has an elongate cross section, so as to allow, for example, the introduction of test strips or the like into the beaker interior without any removal of the beaker contents, or it may be ball-shaped, which would appear to be usually advantageous when the cross-sectional contour of the spout orifice is round.

Furthermore, the closing element may be connected to the spout of the lid edge by means of a link. By this means, the closing element is secured to the associated lid, so that neither the closing element nor the lid can be lost.

These simple measures thus reliably ensure that there cannot occur any obnoxious smells or any impairment of the sterility of the environment on account of the beaker contents before or after the withdrawal of any beaker contents, irrespective of how long it takes before such a filled beaker according to the invention goes to the disposal station after the first withdrawal of any beaker contents.

A further inventive idea contributes to the rationalisation of the laboratory operation generally aimed at by the invention, together with an improvement of the working conditions, which is enhanced to a considerable extent by the last-described measures, according to which idea the lid comprises on its external side a surface area with a preferably rectangular edge contour and having a roughened surface structure. This makes it possible to apply on the visible side of the lid closing the beaker, at a point that can be easily seen, an informatory label containing important information relative to the beaker contents, such as the name of the patient, the date when the urine was taken and the like, in a manner ensuring that the label is not lost, or else to apply on this roughened surface in a suitable manner colour carrier particles in an outline that reproduces the respective information, which may be done, for example, by inscribing. Particularly when the lid is formed from plastics material, which is preferable according to the invention in the same way as the formation of the beaker from plastics material, there arise difficulties with respect to a wipe-resistant direct application of such information on the plastic surface. This last-mentioned inventive idea provides a remedy in an effective manner.

Hereinafter, the invention will be explained in more detail, purely by way of example, with reference to some preferred embodiments shown in the drawings, in which:

FIG. 1 is, in a diagrammatical representation, an axial section through the first embodiment of a beaker according to the invention, with the lid in the working position, FIG. 2 is another embodiment, corresponding to FIG. 1 in its representation, FIG. 3 is yet another embodiment, corresponding to FIGS. 1 and 2 in its representation, FIG. 4 is still another embodiment, corresponding to FIGS. 1 to 3 in its representation, FIG. 5 is an embodiment corresponding to FIGS. 1 to 4 in its representation and having a particularly good stability, FIG. 6 is, on an enlarged scale, a partial section through a first embodiment of a re-closable spout, FIG. 7 is another embodiment of such a spout, corresponding to FIG. 6 in its representation, FIG. 8 is yet another embodiment of such a spout, corresponding to FIGS. 6 and 7 in its representation, FIG. 9 is on an enlarged scale, a cross-sectional detail in the area of the upper edge of the beaker jacket and of the lid edge co-operating therewith in the operating condition, and FIG. 10 is another embodiment of a clamping connection between the lid edge and the beaker edge, corresponding to FIG. 9 in its representation.

The beakers shown in FIGS. 1, 3 and 4 may preferably be of conventional shape, being approximately such as is shown. The beaker shown in FIG. 1 consists, for example, substantially of the beaker jacket 1 and the beaker base 9, which are integrally formed. A lid 2 is connected to the beaker jacket 1 via a link 6, which is preferably fixed by integral moulding. The lid comprises a concavity 3, which projects into the beaker interior in the operating condition, that is to say when the lid 2, which closes the filling orifice of the beaker 1, 9, has been brought into clamping connection with the upper beaker edge. This concavity 3 is bounded by a shoulder 3*a*, which passes along the periphery of the lid 2 and which is drawn upwardly towards the exterior, so that its edge contour corresponds approximately to the contour of the lower end area of the beaker jacket 1, i.e. the area which is near the beaker base. Projecting inwardly from the base surface of the concavity 3 of the lid 2, which corresponds to the lid base 9 in the operating condition and which is not designated, is a chamber-like indentation 4, wherein a spout 5 is arranged, which communicates with the beaker interior and which comprises approximately concertina-like folds, by means of which the base of a superimposed beaker presses this spout 5 into its receiving chamber 4, when the beaker area thereof which engages on the lid 2 of the beaker 1,9 is introduced into the recess 3, while it is possible to return the spout 5 from this position of rest quickly and easily to a position in which it overtops the uppermost edge of the beaker lid 3 by simply pulling it up.

It is evident that while maintaining the known advantages of conventional beakers with respect to easy filling, particularly with urine, and absolute tightness until it is opened for the purpose of withdrawing some of the beaker contents, such a beaker according to the invention offers further advantages with respect to an improvement of the stability of a group of several opened filled beakers, eliminating the risk of the beakers tilting and the beaker contents being spilt or the environment being soiled, despite a small space requirement, and providing at the same time an improvement with respect to the elimination of smells, sterility and hygiene in the treatment of opened filled beakers after the removal of some of the beaker contents, for all that is required before the removal of some of the beaker contents,—without any removal of the lid 2 from the beaker 1,9, which would incidentally be possible, should this be desired—is to pull up the spout 5 in the described manner and to sever its tip, so as to remove some of the beaker contents. Thereafter, it is not even necessary to press this spout 5 by hand back into its reception chamber; on the contrary, it is quite sufficient if the next beaker, from which some of its contents have been withdrawn, is inserted with its area that is near the base into the concavity 3 of the first-mentioned beaker. The contact of the base 9 of the upper beaker 1,9 with the tip of the spout 5 thus brought about not only causes this latter to be plunged into its reception chamber 4 at an adequate depth but also results in an ideal tightness to smells and germs, which virtually suffices to make the environment germ-free and thus the entire operational cycle considerably more hygienic during the time when opened filled beakers have to await their conveyance to the disposal station or the elimination plant (usually an incinerator). Experience has shown that the favourable consequence of the entirety of all these interconnected advantages is a considerable rationalisation of the laboratory test cycle.

In the embodiment shown in FIG. 2, the beaker jacket is designated by 11 and the beaker base by 19. Basically, the beaker jacket 11 has a contour that corresponds to that of the beaker jacket 1 shown in FIG. 1. Only in the area which is opposite to the link connecting the beaker jacket 11 and the lid 12 is there a shortening of its edge 14. This shortening is designed in such a way that it leaves to the upper edge area of the beaker jacket 11, that is to say the area that is close to the lid, an area which preferably goes beyond a semi-circle in cross section and has an edge contour that is in a normal plane to the beaker axis, but has for the rest an indentation contour which is such that in the shortened area 14 the upper edge of the beaker jacket 11 is considerably lower.

Accordingly, the lid 12 is also designed differently. In the area 12*a*, corresponding to the unshortened area of the beaker jacket 11, it comprises a concavity 13 which is bounded in this area, in the same way as described for the concavity 3 shown in FIG. 1, by a shoulder 13*a*, whose internal contour corresponds approximately to the contour of the end area, near the base, of the beaker jacket 11 so that this latter can be well fitted into the space formed by this concavity 13. The beaker base 19 of a beaker placed on, i.e. engaging in the concavity 13 of, the shown beaker 11, 19 would then rest in its peripheral areas on the edge threshold, which is shown but not designated and which bounds the concavity 13 towards the bottom. Free at the base side would be the beaker base of an identical beaker, superimposed on the shown beaker 11, 19, in the shortened area 14. The reason for this is that in this area the lid, too, has a shortened area 12*b*, which follows the edge contour of the shortened area 14 of the beaker jacket 11 so that it can be put all round in sealing clamping engagement with the edge contour thereof. The upper edge of the lid contour is always lower in the shortened area 12*b* than it is in the larger unshortened area 12*a*. Due to the fact that this area 12*a* is larger, an accurate centring of a superimposed beaker is caused, according to the task set, even if the shortened area 12*b* of the lid 12 has no share in this centring. In this shortened area 12*b*, there is arranged near the lid edge, and thus also near the beaker edge, a spout 15, which projects rigidly from the edge contour of the lid 12 and whose free end is sealed by a detachable tip 15*a* and whose interior communicates with the beaker interior, the lower end of the spout 15*a* merging surface-wise in the lid surface 17, which ends, for its part, in the opposite edge contour of the lid 12, preferably in such a way that the superimposition threshold for the base 19 of another superimposed beaker, which engages from the top in the concavity 13, is detented.

The height of the spout 15 is such that it overtops, within its area, the upper edge contour of the shortened area 12*b* of the lid 12 in an adequate manner so as to allow the beaker contents to be poured out properly when its tip 15*a* has been severed, but comes nevertheless still to lie beneath this superimposition threshold, and thus also always beneath the base 19 of a superimposed further beaker, which engages in the concavity 13. It is recognisable that the tasks underlying the invention are effectively solved in this manner, particularly the possibility of superimposing two beakers prior to and after the withdrawal of some of the beaker contents, without any need to design the spout in a special manner, allowing the same to be constructed in the same way and with the same wall thickness as the other areas of the lid 12. This embodiment of the invention thus allows the beaker and lid, including the spout, to be produced as one unit of a plastic moulding, for example by the injection-moulding process, while for the embodiment shown in FIG. 1 a two-part design will be preferred, the beaker and its lid 2, connected thereto through the link 6, being constructed in one piece, approximately in the shaping shown only diagrammatically, the spout with its folds being however prepared in a separate operation and being fixed in a fluid-tight manner in its reception chamber in a further operation.

The embodiment shown in FIG. 3 represents a particularly simple solution of the tasks set to the invention. The beaker jacket thereof is designated by 21 and the beaker base by 29. Its lid 22, which is joined, preferably integrally, to the beaker jacket 21 through a link 26 has approximately a conventional configuration. In the operating condition, the spout 25, with its detachable tip 25*a*, extends from its external side towards the top.

In accordance with the basic task to allow a beaker to be superimposed on the thus formed sealed beaker, a beaker according to this embodiment comprises in its base 29 a recess 27, which corresponds to the contour of the spout 25 and arches inwardly into the vessel interior. It is not absolutely necessary for this recess to correspond to the contour of the spout 25; according to the invention, it suffices if its configuration is such that it is capable of receiving the spout 25 of a beaker in a lower position. In such an event, it is expedient if there are provided on the lid one or more approximately boss-like projections 71 and, in a corresponding co-ordination, a corresponding number of recesses 70 in the beaker base 29, which are engaged when two beakers are superimposed, thus preventing the two beakers not only from being displaced laterally parallel to their base or lid plane but also from being angularly rotated about their common axis. If the contours of the recess 27 are, however, adapted to the spout 25 of the lid 22, such bosses 71, which can be made to engage in recesses 70, may indeed be provided, but they are basically unnecessary, because the centring relative to the two movements mentioned, namely the protection against a translatory displacement and an angular rotation about the common axis, is achieved through the spout 25 of one beaker engaging in the base recess 27 of the other beaker. At this point, it should be noted that one or several corresponding approximately boss-like projections may well be provided, projecting from the external surface of the lid base 29 that is directed downwards, when it would be preferable if the lid base were indented by a corresponding amount towards the interior, while maintaining an edge shoulder, and when there should furthermore be arranged on the lid 22 a corresponding number and arrangement of the recesses which are required for the reception of these boss-like projections and which determine, together with the described projections, the means for the angle-wise association of the lid and beaker.

The construction shown in FIG. 3, where there is provided, in addition to a base recess 27 whose contours are adapted to the spout 25, a pair of at least one approximately boss-like projection 71 on the lid 22 or the beaker 29 and associated therewith a corresponding receiving recess 70 on the other part (beaker base 29 or lid 22), will always be preferable when the spout, which rigidly projects from the external side of the lid beyond the edge contour thereof, has a cross-sectional contour that is rotationally symmetrical to an axis which is approximately normal to the beaker base in the operating condition. In this case, the cross-sectional contour of the spout cannot contribute anything to securing the base of a further beaker which has been superimposed on a beaker standing beneath and having an associated lid that is in the operating condition against rotation. In such a case, there should be provided, in addition to the arrangement in pairs of the spout 25 on the lid 22 and the correspondingly contoured beaker base recess 27, the co-ordination means 70, 71. However, it is preferred by the invention to provide the spouts in known 'per se' manner with a self-centring cross-sectional contour. As shown in all the embodiments, this allows the cross section of the spout to be tapered towards its free end, although this is not at all required for the invention. This taper may be provided in two intersecting planes, which are vertical to the beaker base surface in the operating condition, or in one plane only. The first-mentioned case presents itself, on the one hand, for reasons of a better mouldability when the beaker according to the invention is produced by the injection-moulding method and, on the other hand, because of the simple and economical achievement of an easily manageable and relatively drip-proof spout. Furthermore, the spout may be shaped substantially like a cone or like the frustrum of a cone. Such a design is known. It is also known to design the spout as a cone or frustrum of a cone having an elongate base surface. These spout designs, which are known 'per se' but are provided on conventional beakers of this type without any discernible reason, gain new and momentous importance in connection with the invention and its respective specific inventive ideas respectively.

However, it has turned out to be particularly preferable if the spout is designed as a pyramid or frustrum of a pyramid. Advantageously, it may be designed as a pyramid or frustrum of a pyramid which is oblique on its base surface. For an easier understanding, this is not shown in any of the embodiments illustrated, but can be easily imagined. For example in FIG. 3, the wall of the spout 25 pointing towards the lid edge that is remote from the link needs to be formed approximately vertically to the lid surface, the opposite spout wall then having a more pronounced inclination. Known beakers of this type have an obliquity of the spout in exactly the opposite direction i.e. the inclination of their spout wall on the link side is steeper than that of the spout wall on the beaker edge side. But even such a known oblique design of the spout lies within the scope of the idea underlying the invention, which is directed at a particularly good and hygienic guidance of the jet of the fluid contents to be removed from the beaker interior.

The embodiment shown in FIG. 4 is based on the design shown in FIG. 3 and utilises, for an improved and more reliable centring and securing of two superimposed beakers against a translatory displacement and an angular rotation, a measure which has already been described in connection with FIG. 1. Thus, the beaker shown in FIG. 4, with its beaker jacket 31 and the beaker base 39, comprising the recess 37, as well as the preferably integrally formed connecting link 36 to the lid 32, corresponds entirely to the design shown in FIG. 3. The only difference from the embodiment shown in FIG. 3 is the design of the lid. This lid 32 has a concavity 33, which corresponds approximately to the concavity 3 shown in FIG. 1 and whose internal contour is again defined by an edge shoulder 33*a*, whose contour corresponds to the area of the beaker jacket 31 near the base. From the base of this concavity 33 rises, in the same way as described for FIG. 3 with respect to the external plane of the lid 22, the spout 35, which is rigid in itself and whose orifice is sealed by a detachable tip 35*a* in the same way as described for the preceding embodiments.

It is discernible that in this instance the co-ordinating means shown in FIG. 3, with its arrangement in pairs of an approximately boss-like projection on one part and a receiving recess therefor on the other part can be dispensed with, because the co-ordinating means is formed by the combination of the receiving recess 37 in the beaker base 39 or its contour-wise agreement with the spout 35 arranged on the lid 32 and the concavity 33 in the lid 32. This is therefore a particularly simple and economical development of the invention to achieve the properties of a beaker according to the invention as required by the tasks set.

For each of the embodiments shown in FIGS. 1 to 4 it is provided that the filling orifice of the beaker 1,9 and 11,19 and 21,29 and 31,39 respectively has an edge contour that is larger than that of the beaker base 9 and 19 and 29 and 39 respectively, that is to say that the beaker jacket 1 and 11 and 21 and 31 respectively converges towards the associated beaker base 9 and 19 and 29 and 39 respectively. Depending on the degree to which the respective beaker is filled, in consideration of the ratio of the size of the beaker base standing surface and the beaker jacket height, a greater or lesser stability of the filled beaker is given. For an identical beaker jacket height, and even for an identical capacity irrespective of the latter, the stability of the embodiment shown in FIG. 5 is better by comparison, this embodiment fulfilling, however, likewise the requirements to be met by the invention. In this embodiment according to FIG. 5, the filling orifice of the beaker, which is formed by the beaker jacket 41 and the base 49, has an edge contour that is smaller than that of the beaker base 49, that is to say the beaker jacket 41 does not converge towards the beaker base 49 but converges towards the lid 42, which may incidentally be connected to the beaker jacket 41 via a preferably integrally formed link 46, as described in conjunction with the embodiments shown in FIGS. 1 to 4. Apart from the smaller edge contour, the lid 42 of the embodiment shown in FIG. 5 is for the rest similar in design to the lid 22 shown in FIG. 3. It comprises a spout 45, which is arranged close to its edge and is provided with a detachable tip 45*a* sealing it.

In this embodiment, the concavity enabling two beakers, whose lids are applied in their operating condition and which are provided with an open or closed spout, according to the invention, to be put together is arranged in the beaker base 49. According to a subordinate inventive idea, the beaker base 49 comprises an inwardly drawn-up shoulder 43*a*, which extends along its periphery and which has an internal contour that corresponds approximately to the end area of the beaker jacket 41 close to the lid. This allows the entire beaker area which is near the lid and covered by the lid to be accommodated in the concavity 43 with the recess 47, including the lid 42 and its spout 45, the uppermost beaker being placed from the top on the tip of the lower beaker 41,49, which is covered by its lid 42. The internal contour of the recess 43 is such that the lid of the other beaker can also be accommodated therein. In such a case, where the lid 42 is connected to the beaker jacket 41 via a link 46, two measures can alternatively be taken, namely either to attach the connecting end of the connecting link 46 between the lid 42 and the beaker jacket 41 on the lid side so low that it need not enter the concavity 43 or to extend the edge of the recess 43 to such an extent that the shown arrangement of the connecting link 46 can be accommodated therein when two beakers are put together.

It is discernible that due to the different shaping of the beaker shown in FIG. 5 its production in plastics material is advantageously not effected by injection-moulding, but is effected, with a selection of suitable plastics material, for example by the blowing method or another coreless manufacturing method.

In all the embodiments outlined so far the spout 5 and 15 and 25 and 35 and 45 respectively of the lid 2 and 12 and 22 and 32 and 42 respectively has been described as having in each case a separable tip, that is to say a tip which is integrally formed in its condition of non-use and which cannot be attached again when the spout is opened. The disadvantages of such a non-sealable spout of the conventional type, which may have been reduced to a considerable extent by the invention, are described at the beginning. However, in order to remedy this situation in a simple and cheap and yet very effective manner, there may be provided one of the designs shown in FIGS. 6 to 8, enabling the orifice of the spout to be opened and closed as often as it is desired. According to a subordinate inventive idea, the spout is sealed in each case in a fluid-tight manner by means of a closing element which can be removed and returned to its operating position. In the embodiments shown in FIGS. 6 to 8 the closing elements are shown on the same lid part, namely the lid part 32 shown in FIG. 4. This means that the associated spouts are in each case different in design with respect to their internal cross-sectional development but are identical with respect to their external contours and are therefore all designated by 35.

In FIG. 6, there is placed on the free end of the spout 35 of the lid 32 a clamping cap 50, which can be removed and replaced in a fluid-tight manner as often as it is desired and which is connected through a link 51 either to the lid edge, as would be advantageous, for example, in a construction according to FIG. 5, or to the edge of the spout itself.

This clamping cap 50 thus seals the free end of the spout 35 by engaging over the latter and covering the orifice thereof at the front end.

In FIG. 7, there is shown a different constructional form of a closing element, which does not engage over the free end of the spout 35, but engages in its orifice in a plug-like manner. For this purpose, there is provided a plastics material strip 52, which tapers slightly towards its free end and which can be introduced into the spout 35 orifice, which has not been designated, in a tightly clamping and fluid-tight manner. This plug, which is preferably shaped like a strip but may be designed approximately like a needle, is also connected via a corresponding connecting link 53 either to the lid edge or to the spout wall, and this connection is expediently integral. In the embodiment shown in FIG. 8, the design of the closing element, which is also introduced into the orifice of the spout 35, has been modified. This embodiment is to be preferred for cross-sectional shapes of the spout orifice which are symmetrical with respect to their cross section. However, there may well be employed in a useful manner closing elements which are roller-like in design, possibly as a cylinder of approximately circular cross section whose axis is parallel to the longitudinal alignment of the spout, for the purpose of closing an elongate cross section of the spout. This closing element 54, shown in FIG. 8, is also connected via a link-like connecting element 55 either to the lid edge or the spout wall in the manner already described.

At this point, it is emphasized that, for a better clarity, the embodiments shown in FIGS. 6 to 8 proceed from the assumption that there are involved spouts of a lid as shown in FIG. 4, the corresponding areas of the lid, if shown, as well as the shown cross-sectional areas of the spouts thus being marked 32 and 35 respectively. However, these embodiments of the invention of closing elements for the spout of a beaker according to the invention can be used similarly for any other development of a beaker lid or its spout, for example in conjunction with one of the spouts shown in FIGS. 1 to 3 and 5 and described hereinbefore.

Furthermore emphasized is the fact that in all the embodiments the spouts shown are advantageously of greater length in their cross-sectional edge contour, in the direction that is transversal to the drawing plane, than is shown in the drawing plane. This means that the spout has an elongate cross-sectional contour in a section conducted in the operating condition parallel to the lower edge contour of the beaker base, which determines the standing surface of the beaker. The advantage of such a cross-sectional design of the spout lies in the fact that this allows the orifice also to be given, in an economical manner, an elongate, preferably narrow rectangular cross-sectional contour, which is particularly suitable for the introduction of test strips into the beaker interior without any removal of the beaker contents.

Two preferred types of clamping connections between the lid and beaker jacket are shown in FIGS. 9 and 10, and this is done for simplicity's sake with the aid of a cross-sectional detail through the embodiment shown in FIG. 1. The corresponding clamping connection might be used in the same way in all the other embodiments. In each case, the beaker edge and the associated portion of the lid edge comprise a known 'per se' sealing device, which is in clamping engagement therewith in the operating condition and which seals the beaker interior in a fluid-tight manner. In the case of the embodiment shown in FIG. 9, this device is formed by two encircling beads, which engage over one another in a clamping manner, on the two parts that are to be clamped together. On the one hand, the beaker jacket 1 comprises on its upper edge, which is close to the lid, an outwardly directed bead 61, over which a bead 62, which is secured to the lid and projects from the edge of the lid surface 2, can be pushed in a ring-like manner so that it engages behind and under the bead 61, which is secured to the beaker jacket. By this means, there is provided a reliable fluid-tight clamping connection between the beaker and lid.

A surprising effect occurs in the embodiment shown in FIG. 10. The upper edge of the beaker jacket 1, which is near the lid comprises an inwardly directed bead 63 and beneath it an annular recess widening 65, which is located on the inside of the beaker jacket 1. The lid 2 has, for its part, an edge contour which is approximately hat-shaped in cross section and whose internal annular member engages in the annular groove 65 of the beaker wall, while its external likewise annular member 64 engages over the uppermost edge of the beaker jacket 1, including the inwardly directed bead 63 thereof. For better clarity, the annular gap between the two lid members is shown in FIG. 10 in a size so that a clearance towards the beaker jacket 1 is provided on either side thereof. In practice, the annular gap between the two lid members will be provided in such a way that when the lid 2 is pushed on the upper edge of the beaker jacket 1, the latter is deformed in a sealing manner approximately towards the interior, so that the annular groove 65 acts as the point of weakening which determines the deformation in a suitable manner. In any event, the surprising result of production-wise experience is that in a construction as that shown in FIG. 10 there can always be achieved a well-fitting fluid-tight clamping connection between the lid and beaker without any requirement for accurate dimensional tolerances in the associated parts of the edge-wise clamping connection between the beaker jacket and the lid.

Like any other suitable clamping connection, these two shown embodiments of clamping connections between the beaker and lid can be used in conjunction with any desired embodiment of the invention. Furthermore, the purely diagrammatically shown cross-sectional forms of the beaker and lid may have a rotationally symmetrical design, for example a circular design, or else an approximately elliptical or egg-shaped contour and finally, and even preferably, a polygonal contour. If the beaker and, adapted thereto, the associated lid have, for example, a hexagonal cross-sectional contour, there results a particularly favourable space utilisation of the filled beakers, which must be held in a waiting position when some of the beaker contents have been withdrawn for the performance of the respective laboratory tests. However, a rectangular cross-sectional contouring has also proved to be advantageous, since it provides a simple possibility of effecting a designed alignment with simple and economical means on automatic conveyors. A square cross-sectional contour has given particularly satisfactory results.

At this point, it is emphasised that a beaker according to the invention may basically be made from any suitable material. There may well be applications where a construction in metal would be preferable. However, most applications will be served successfully and cheaply by a plastics material construction. On the other hand, it is however also possible to use, for very specific applications, a beaker according to the invention which is formed from material containing, for example, cellulose and which is then advantageously covered by a layer which seals its wall surfaces and which may be applied, for example, by the plastics material dipping method. However, preferred is a beaker according to the invention in plastics material.

Irrespective of the fact whether this material has been moulded by the injection-moulding method or by a coreless moulding method, such as a blowing method, it always has the property, considered to be particularly advantageous in the majority of applications, that the surface of the moulded part is repellent to any adherence of any type of foreign body. However, this may cause trouble for the invention with respect to a very specific point. This relates to the necessity of providing beakers according to the invention, for example such which are associated with very specific properties of their contents, such as the sex, age, time when the specimen was taken, the illness and similar matters concerning a patient, with information on these data characterising the beaker contents at a suitable location on the external surface of the beaker. But, without any special measures being taken, this is positively prevented when the beaker and/or the lid is designed in plastics material. In order to remedy this situation, that is to say to provide the possibility of recording the necessary information on the wall of the vessel according to the invention in a suitable manner, so that it is not wiped off or is otherwise made illegible or reduced in discernibility, a further inventive idea provides for the arrangement of a surface area having preferably a rectangular, that is to say plate-like edge contour with a roughened surface structure on the external side of the lid and/or the beaker jacket. In the embodiment according to FIG. 2, such an area 18 with a roughened surface structure is shown in the obliquely ascending lid wall area 17. An embodiment according to FIG. 2 is particularly suitable for an approximately desk-like arrangement of such an information carrier on the surface area 18 with the roughened surface structure or for the application of a corresponding colour-particle layer having the contour of written characters. For the rest, reference is made to the fact at this point that although only FIG. 2 shows such an information carrier area 18, on which there may be applied, for example, a self-adhesive label containing information on the visual side thereof or else coloured particles made by a suitable manufacturer of written characters, such information carrier areas may also be provided in the same manner at a suitable location in the other embodiments shown, both on the outside of the lid thereof and on the beaker jacket thereof and, if required, even on the beaker base thereof.

Although the invention has been described in detail with reference to some preferred embodiments, it is not confined to these. On the contrary, there are open to the expert manifold possibilities of adapting the invention, by a suitable different combination of its features or by exchanging them for equivalent means, to the respective constructional factors or the requirements of the individual application, without departing from the scope of the invention.

I claim:

1. A stackable beaker for laboratory purposes, particularly a urine container, having a cover which is provided in the vicinity of its edge with a spout, said cover on its outward side, from which said spout is projecting, having a surface corresponding generally in size and shape to the beaker jacket edge area near the beaker base to facilitate nesting and stacking of one beaker on top of another beaker when the beakers are closed by the covers thereof, the spout in the stacking position being contained in a chamber provided on said cover or said beaker base, and means being provided for releasably fixing the angular association of beakers stacked or stored, respectively, over each other.

2. A beaker as claimed in claim 1, characterised in that the lid comprises an outwardly drawn-up shoulder, which encircles the lid periphery and which has an internal contour that corresponds approximately to the beaker jacket end area near the beaker base.

3. A beaker as claimed in claim 1, characterised in that the beaker base comprises an inwardly drawn-up shoulder, which encircles the base periphery and which has an internal contour that corresponds approximately to the beaker jacket end area near the lid.

4. A beaker as claimed in claim 1 characterised in that the lid comprises an approximately chamber-like indentation, which is open towards the exterior and into which a spout, which can be folded approximately like a concertina, is lowered in its condition of rest and from which it can be extracted towards the exterior for its operating condition.

5. A beaker as claimed in claim 1, comprising a spout which projects rigidly from the outside of the lid, characterised in that the beaker jacket comprises a shortened area over a partial area of its periphery on its upper edge near the lid and in that the lid comprises an area which corresponds with respect to the size of its centre angle to the unshortened area of the beaker jacket and which comprises a concavity whose edge contour is formed by an encircling and outwardly drawn-up shoulder, having an internal contour that corresponds approximately to the beaker jacket area near the base, as well as an area which corresponds to the beaker jacket shortened area and in which there is arranged a spout which terminates with its free end beneath the lower limitation of the shoulder in this lid area, which corresponds to the unshortened area of the beaker jacket, but above the lid area corresponding to the beaker jacket area comprising the shortening and whose lower end merges surface-wise in the lid surface which ends in the opposite edge contour of the lid.

6. A beaker as claimed in claim 1, comprising a spout which projects rigidly from the lid edge contour, characterised in that the beaker base comprises a concavity, which corresponds to the spout area projecting from the lid edge contour when the lid is placed on the beaker in a sealing manner, the concavity being vertical beneath the spout.

7. A beaker as claimed in claim 1, characterised in that the cross section of the spout tapers towards the free end of the spout at least in a plane containing the central axis of the beaker in the operating condition.

8. A beaker as claimed in claim 7, characterized in that the spout is of conical shape.

9. A beaker as claimed in claim 7, characterized in that the spout is provided with an elongate base surface.

10. A beaker as claimed in claim 7, characterized in that the spout is shaped like a pyramid.

11. A beaker as claimed in claim 10, characterized in that the spout is oblique over its base surface.

12. A beaker as claimed in claim 11, characterized in that the spout has an elongate cross-sectional contour in a section conducted in the operating condition parallel to the lower edge contour of the beaker base.

13. A beaker as claimed in claim 1, characterized in that the beaker edge and the associated part of the lid edge each comprise a closing device, which are in clamping engagement and seal the beaker interior in a fluid-tight manner.

14. A beaker as claimed in claim 13, characterised in that the closing device is formed by a bead which is arranged along the beaker edge and which is clamped in the operating condition with a lid edge contour, which is approximately hat-shaped in cross section, in a fluid-tight manner.

15. A beaker as claimed in claim 1, characterized in that the lid is connected to the beaker by means of a link.

16. A beaker as claimed in claim 1, characterized in that the beaker has a filling orifice with an edge contour that is smaller than that of the beaker base.

17. A beaker as claimed in claim 1, characterized in that the beaker has a filling orifice with an edge contour that is smaller than that of the beaker base.

18. A beaker as claimed in claim 1, characterized in that it has a round cross-sectional contour.

19. A beaker as claimed in claim 1, characterized in that it has an approximately elliptical cross-sectional contour.

20. A beaker as claimed in claim 1, characterized in that it has a polygonal cross-sectional contour.

21. A beaker as claimed in claim 1, characterized in that the beaker and the lid are formed from a plastic material.

22. A beaker as claimed in claim 1, characterized in that the spout has a moulded-on, detachable tip.

23. A beaker as claimed in claim 1, characterised in that the spout is sealed in a fluid-tight manner by means of a detachable closing element, which can be returned to its operative position.

24. A beaker as claimed in claim 23, characterised in that the closing element is a clamping cap covering the free end of the spout.

25. A beaker as claimed in claim 23, characterised in that the closing element is a plug which is inserted into the free end of the spout orifice.

26. A beaker as claimed in claim 25, characterised in that the plug is designed as a strip which tapers slightly towards its free end.

27. A beaker as claimed in claim 25, characterised in that the closing strip is approximately ball-shaped in design.

28. A beaker as claimed in claim 23, characterised in that the closing element is connected to the spout or the lid edge by means of a link.

29. A beaker as claimed in claim 1, characterised in that the lid and the beaker jacket have on their outside a surface area with a preferably rectangular edge contour and a roughened surface structure.

30. A beaker as claimed in claim 1 wherein the lid has on its external side, from which the spout projects, a concavity which corresponds in size and shape approximately to the beaker jacket edge area near the beaker base.

31. A beaker as claimed in claim 1 wherein the beaker has a base with a concavity corresponding in size and shape approximately to the external side of the lid.

32. A beaker as claimed in claim 1 characterized in that the means for the angular coordination of the lid and beaker, comprises at least one inwardly directed concavity on the lid and, corresponding thereto, at least one projection on the beaker base.

33. Beaker according to claim 1, in which said means for the angular association of beakers stacked or stored, respectively, over each other comprises at least one projection and/or at least one recess directed to the interior at said cover and correspondingly at least one recess and/or at least one projection at the beaker bottom.

34. Beaker according to claim 33, in which the projection determining the angular association of beakers stacked or stored, respectively, over each other is provided by the region of the rigid spout projecting over the edge contour of said cover.

* * * * *